United States Patent
Bower et al.

(10) Patent No.: US 10,347,785 B2
(45) Date of Patent: Jul. 9, 2019

(54) DEVICE FOR EMITTING AND DETECTING PHOTONS AND METHOD OF PRODUCING THE SAME

(71) Applicant: Nokia Technologies Oy, Espoo (FI)

(72) Inventors: Chris Bower, Cambridge (GB); Piers Andrew, Cambridge (GB); Richard White, Cambridge (GB)

(73) Assignee: NOKIA TECHNOLOGIES OY, Espoo (FI)

(*) Notice: Subject to any disclaimer, the term of this patent is extended or adjusted under 35 U.S.C. 154(b) by 0 days.

(21) Appl. No.: 15/736,967

(22) PCT Filed: May 18, 2016

(86) PCT No.: PCT/FI2016/050332
§ 371 (c)(1),
(2) Date: Dec. 15, 2017

(87) PCT Pub. No.: WO2016/207483
PCT Pub. Date: Dec. 29, 2016

(65) Prior Publication Data
US 2018/0190854 A1    Jul. 5, 2018

(30) Foreign Application Priority Data
Jun. 24, 2015   (EP) ..................... 15173574

(51) Int. Cl.
*H01L 31/12*   (2006.01)
*H01L 31/028*  (2006.01)
(Continued)

(52) U.S. Cl.
CPC .......... *H01L 31/125* (2013.01); *A61B 5/0077* (2013.01); *A61B 5/02416* (2013.01);
(Continued)

(58) Field of Classification Search
CPC ......... H01L 31/145–153; H01L 31/125; H01L 31/165–173; H01L 33/00–648;
(Continued)

(56) References Cited

U.S. PATENT DOCUMENTS

| | | |
|---|---|---|
| 5,247,193 A | 9/1993 | Menda |
| 7,598,949 B2 | 10/2009 | Han |
| (Continued) | | |

FOREIGN PATENT DOCUMENTS

| | | |
|---|---|---|
| EP | 1840983 | 10/2007 |
| JP | 2010-153793 A | 7/2010 |
| (Continued) | | |

OTHER PUBLICATIONS

International Search Report and Written Opinion received for corresponding Patent Cooperation Treaty Application No. PCT/FI2016/050332, dated Oct. 11, 2016, 18 pages.
(Continued)

*Primary Examiner* — Tucker J Wright
(74) *Attorney, Agent, or Firm* — Alston & Bird LLP

(57) ABSTRACT

A single device for emitting and detecting photons. The device comprises a semiconductive layer (3), active material (5), further dielectric layer (17) and overlying electrode (25). In a first mode of operation an electrical field is applied between the semiconductive layer (3) and the overlying electrode (25). This enables photons to be emitted from the active material (5). In a second mode of operation, the semiconductive layer (3) constitutes a channel of a field effect transistor (23). The field effect transistor further comprises source electrode (11), drain electrode (15), gate electrode (13) and dielectric layer (19). Photons absorbed by the active material (5) causes charge to be transferred to the semiconductive layer (3), thereby changing the channel resistance. A plurality of such devices can be arranged in a configurable array.

20 Claims, 5 Drawing Sheets

Figure 1:
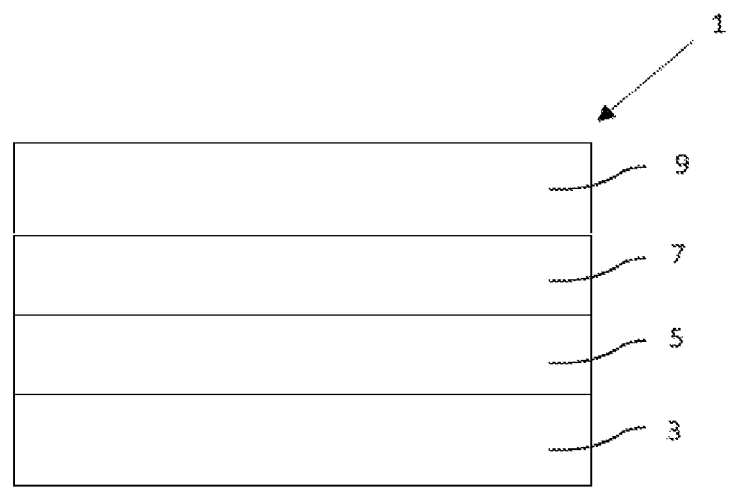

(51) Int. Cl.
| | |
|---|---|
| *H01L 27/144* | (2006.01) |
| *H01L 31/0352* | (2006.01) |
| *A61B 5/00* | (2006.01) |
| *A61B 5/024* | (2006.01) |
| *H01L 33/00* | (2010.01) |
| *H01L 27/15* | (2006.01) |
| *H01L 31/18* | (2006.01) |
| *H01L 33/34* | (2010.01) |
| *A61B 5/02* | (2006.01) |
| *A61B 5/1455* | (2006.01) |

(52) U.S. Cl.
CPC ........ *A61B 5/7485* (2013.01); *H01L 27/1446* (2013.01); *H01L 27/156* (2013.01); *H01L 31/028* (2013.01); *H01L 31/035218* (2013.01); *H01L 31/1804* (2013.01); *H01L 33/0041* (2013.01); *H01L 33/0054* (2013.01); *H01L 33/34* (2013.01); *A61B 5/02* (2013.01); *A61B 5/1455* (2013.01); *A61B 2562/0233* (2013.01); *A61B 2576/00* (2013.01); *Y02E 10/547* (2013.01)

(58) Field of Classification Search
CPC ......... H01L 27/15–156; H01L 2933/00–0091; H01L 33/0041; F21K 9/00–278
See application file for complete search history.

(56) References Cited

U.S. PATENT DOCUMENTS

| | | |
|---|---|---|
| 8,320,423 B2 | 11/2012 | Stern |
| 8,872,778 B2 | 10/2014 | Smith et al. |
| 2003/0222198 A1 | 12/2003 | Olszak et al. |
| 2004/0208415 A1 | 10/2004 | Kim et al. |
| 2008/0186260 A1 | 8/2008 | Lee |
| 2010/0065834 A1 | 3/2010 | Hammond |
| 2010/0200849 A1 | 8/2010 | Okai et al. |
| 2011/0175060 A1 | 7/2011 | Okai et al. |
| 2014/0340436 A1 | 11/2014 | Kumeta et al. |

FOREIGN PATENT DOCUMENTS

| | | |
|---|---|---|
| JP | 2011-168473 A | 9/2011 |
| JP | 2012-138451 A | 7/2012 |
| JP | 2013-129548 A | 7/2013 |
| WO | WO-2005/104075 A2 | 11/2005 |

OTHER PUBLICATIONS

Klekachev Alexander V. et al. "Charge transfer effects in graphene-CdSe/ZnS quantum dots composites", Proceedings of SPIE, SPIE-International Society for Optical Engineering, US, vol. 8462, Sep. 27, 2012, p. 84620L.

Cicoira F. et al. "Organic Light Emitting Field Effect transistors: Advances and Perspectives", Advanced Functional materials, Wiley-V.C. H. Verlag GmbH & Co. KGAA, DE, vol. 17, No. 17, Nov. 23, 2007 pp. 3421-3434.

Extended European Search Report for Application No. 15173574.3 dated Jan. 22, 2016, 11 pages.

Seo et al. "Fully Transparent Quantum Dot Light-Emitting Diode Integrated with Graphene Anode and Cathode", ACS Nano, Nov. 26, 2014, pp. 1-7.

Cho et al. "High Performance AC Electroluminescence from Colloidal Quantum Dot Hybrids", Adv. Mater. 2012, 24, pp. 4540-4546.

Bozyigit et al. "Challenges and Solutions for High Efficiency Quantum Dot-Based LEDs", MRS Bulletin, vol. 38, Sep. 2013, pp. 731-736.

Stern, "Design of a Silicon Avalanche Protodiode Pixel with Integrated Laser Diode Using Black-Illuminated Crystallographically Etched Silicon-on-Sapphire with Monolithically Integrated Microlens for Dual-Mode", SPIE NanoScience & Engineering, vol. 7780, Aug. 18, 2010, pp. 1-16.

Japanese Office Action for Application No. 2017-567242, dated Feb. 27, 2019, 8 pages.

DEVICE FOR EMITTING AND DETECTING PHOTONS AND METHOD OF PRODUCING THE SAME

RELATED APPLICATION

This application was originally filed as PCT Application No. PCT/FI2016/050332 filed May 18, 2016, which claims priority benefit from EP Application No. 15173574.3, filed Jun. 24, 2015.

TECHNOLOGICAL FIELD

Examples of the present disclosure relate to an apparatus and method of providing an apparatus for emitting and detecting photons. In particular, they relate to an apparatus and method of providing an apparatus for emitting and detecting photons which can be provided within a configurable array.

BACKGROUND

Photon detectors are used in a wide variety of applications. For instance, a photon detector may be used to make absorption measurements or detect interruption of a light signal. In some examples the photon detector may require a photon emitter to be provided in addition to the detector. In such examples this will require two discrete components, a photon emitter and a photon detector, which are packaged separately. This will provide limitations on the resolution of an array of such photon detectors.

It is useful to provide improved photon detector devices.

BRIEF SUMMARY

According to various, but not necessarily all, examples of the disclosure there may be provided an apparatus comprising: an active material positioned between a semiconductive layer and a conductive layer; wherein the semiconductive layer and the conductive layer are configured such that in a first mode of operation the active material acts as a photon emitter and in a second mode of operation the active material acts as a photon detector.

In some examples in the first mode of operation an electric field may be applied between the semiconductive layer and the conductive layer.

In some examples the semiconductive layer may be connected to a source electrode and a drain electrode such that in the second mode of operation the semiconductive layer provides a channel within a field effect transistor.

In some examples the semiconductive layer and the conductive layer may be arranged such that the apparatus can be configured in the first mode of operation at a first time and in the second mode of operation at a second, different time.

In some examples the active material may comprise quantum dots.

In some examples the semiconductive layer may comprise graphene. The graphene may form a graphene field effect transistor.

In some examples a dielectric layer may be provided between the active material and the conductive layer.

In some examples a hole transport layer may be provided between the active material and the semiconductive layer.

In some examples an electron transport layer may be provided between the active material and the conductive layer.

In some examples the apparatus may comprise a barrier configured to prevent illumination from an adjacent apparatus.

In some examples the apparatus may comprise a microlens array or fibre optic faceplate configured to prevent illumination from an adjacent apparatus.

In some examples the apparatus may comprise control circuitry configured to control the mode of operation of the apparatus.

According to various, but not necessarily all, examples of the disclosure there may be provided an array comprising a plurality of apparatus as described above.

In some examples a first subset of the plurality of apparatus may be configured in the first mode of operation and a second subset of the plurality of apparatus may be configured in the second mode of operation.

In some examples at least one apparatus may be arranged within different subsets at different times.

According to various, but not necessarily all, examples of the disclosure there may be provided a method comprising: providing an active material between a semiconductive layer and a conductive layer; and configuring the semiconductive layer and the conductive layer such that in a first mode of operation the active material acts as a photon emitter and in a second mode of operation the active material acts as a photon detector.

In some examples in the first mode of operation an electric field may be applied between the semiconductive layer and the conductive layer.

In some examples the semiconductive layer may be connected to a source electrode and a drain electrode such that in the second mode of operation the semiconductive layer provides a channel within a field effect transistor.

In some examples the method may comprise configuring the active material in the first mode of operation at a first time and in the second mode of operation at a second, different time.

In some examples the active material may comprise quantum dots.

In some examples the semiconductive layer may comprise graphene. The graphene may form a graphene field effect transistor.

In some examples the method may comprise providing a dielectric layer between the active material and the conductive layer.

In some examples the method may comprise providing a hole transport layer between the active material and the semiconductive layer.

In some examples the method may comprise providing an electron transport layer between the active material and the conductive layer.

In some examples the method may comprise providing a barrier configured to prevent illumination from an adjacent apparatus.

In some examples the method may comprise providing a microlens array or fibre optic faceplate configured to prevent illumination from an adjacent apparatus.

In some examples the method may comprise configuring control circuitry to control the mode of operation of the active material.

In some examples the method may comprise providing an array wherein the array comprises a plurality of apparatus as described above.

In some examples the method may comprise configuring a first subset of the plurality of apparatus are configured in a first mode of operation and a second subset of the plurality of apparatus are configured in a second mode of operation.

In some examples the method may comprise configuring at least one apparatus within different subsets at different times.

According to various, but not necessarily all, examples of the disclosure there may be provided examples as claimed in the appended claims.

BRIEF DESCRIPTION

Figure 2:
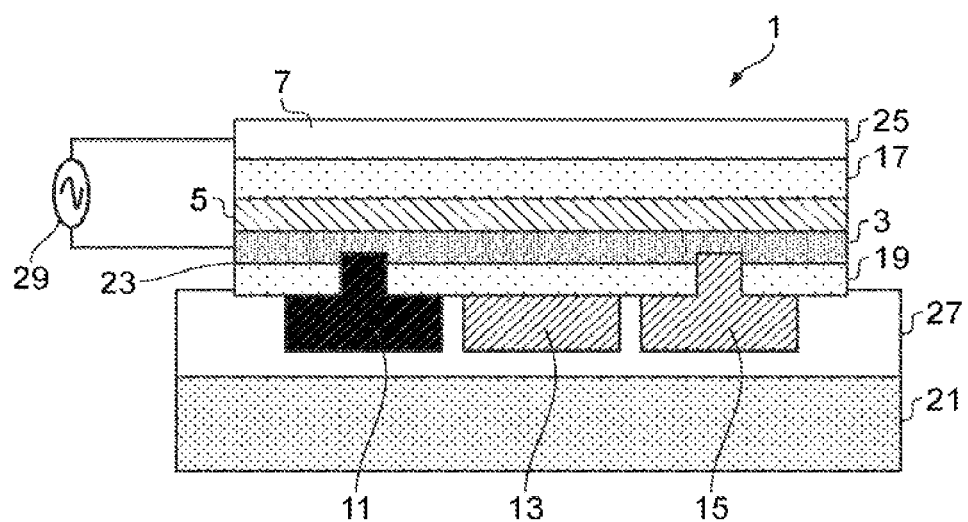
Figure 3:
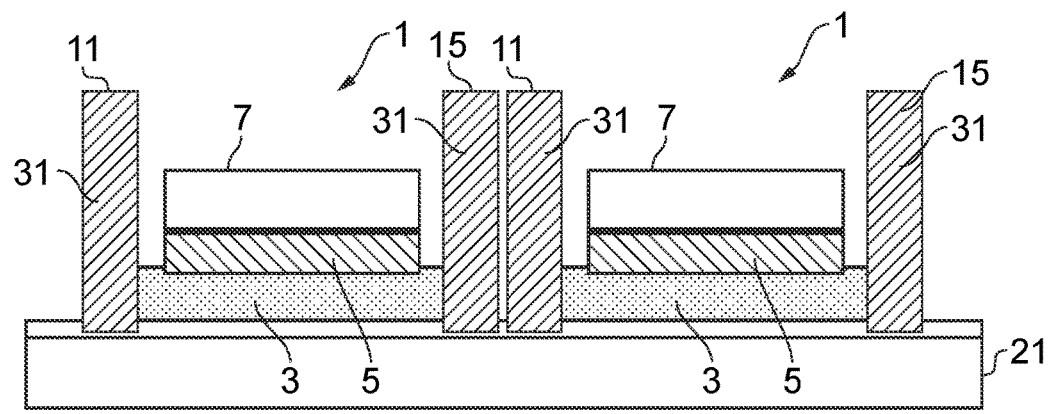
Figure 4:
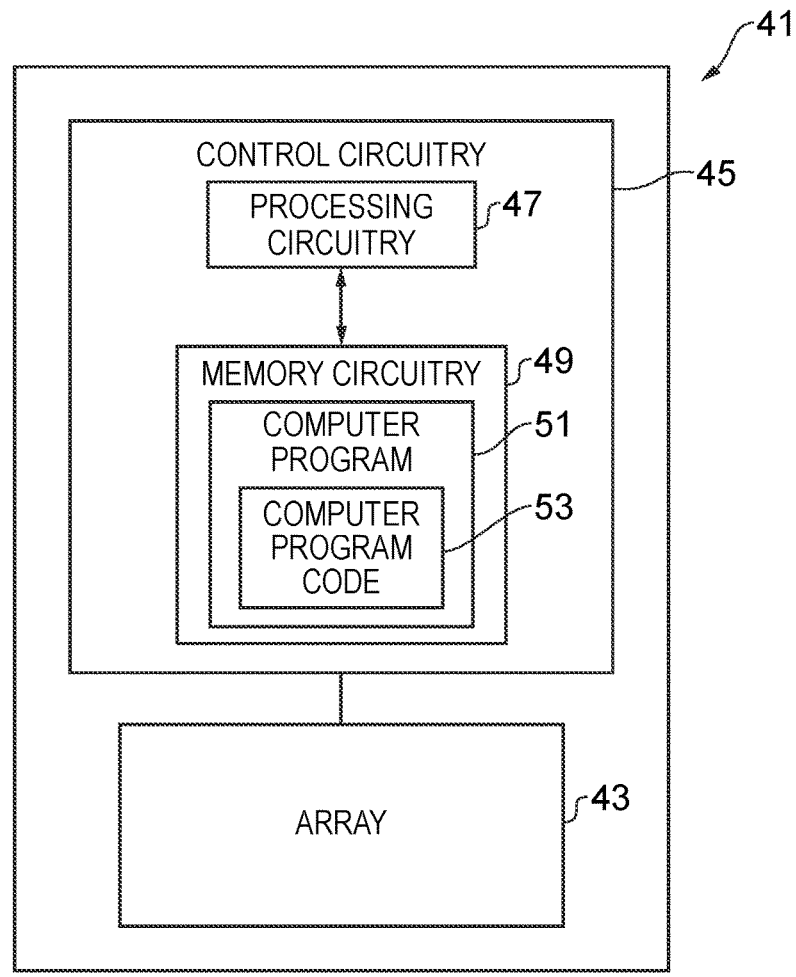
Figure 5A:
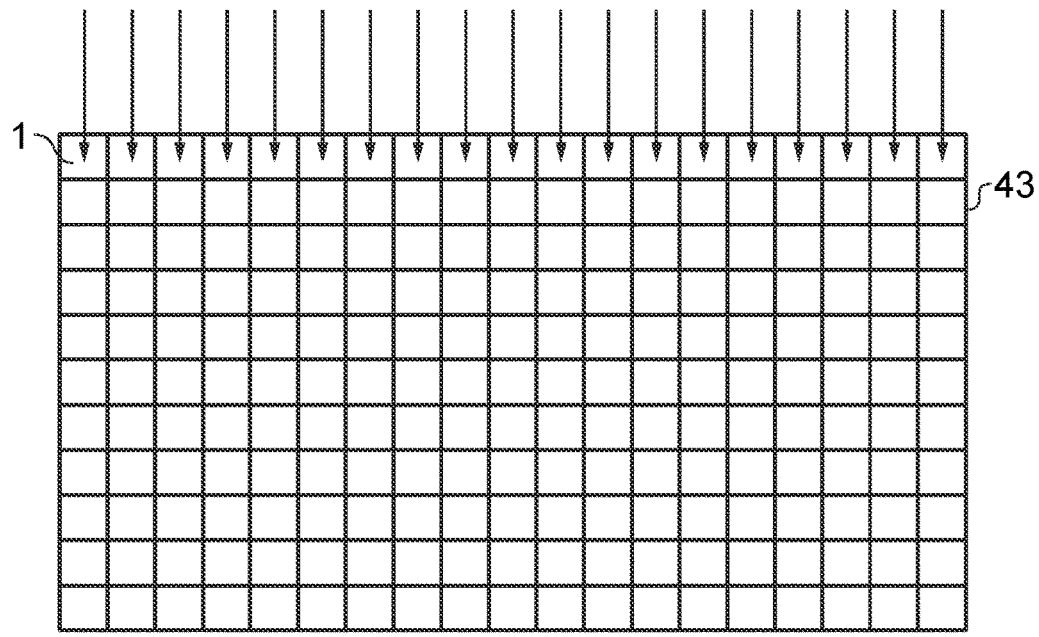
Figure 5B:
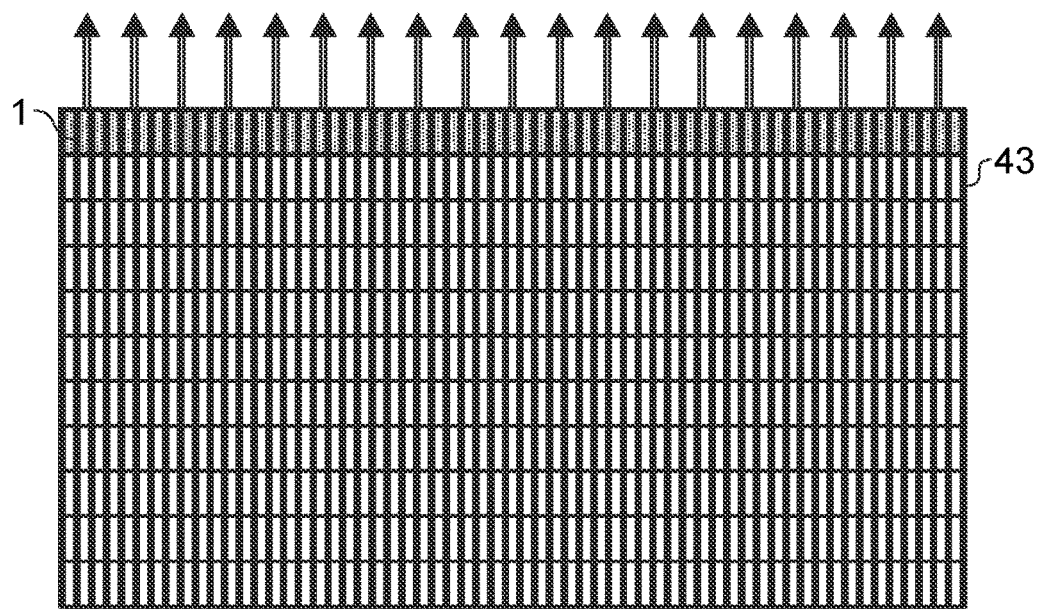
Figure 6A:
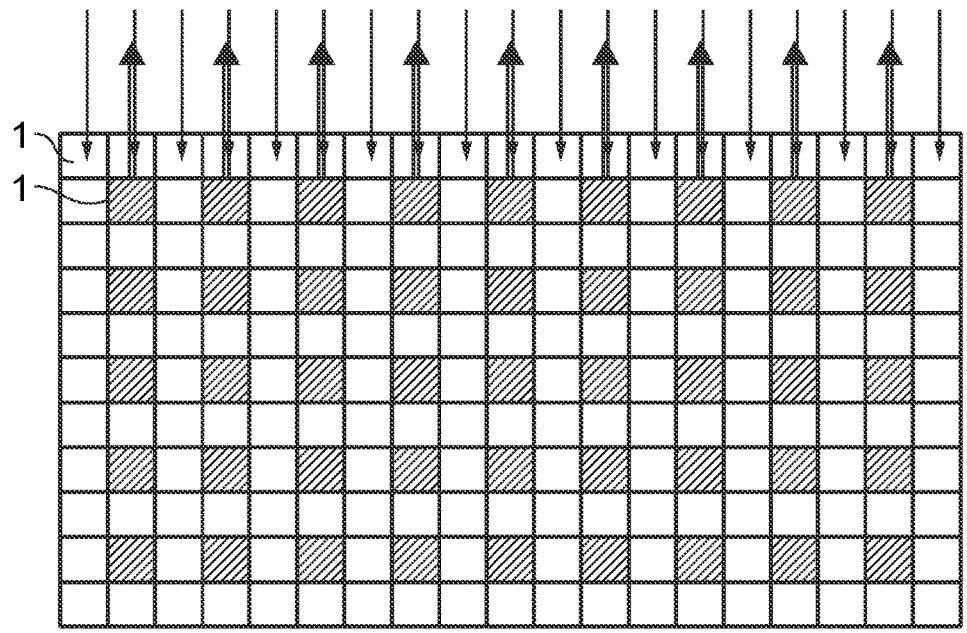
Figure 6B:
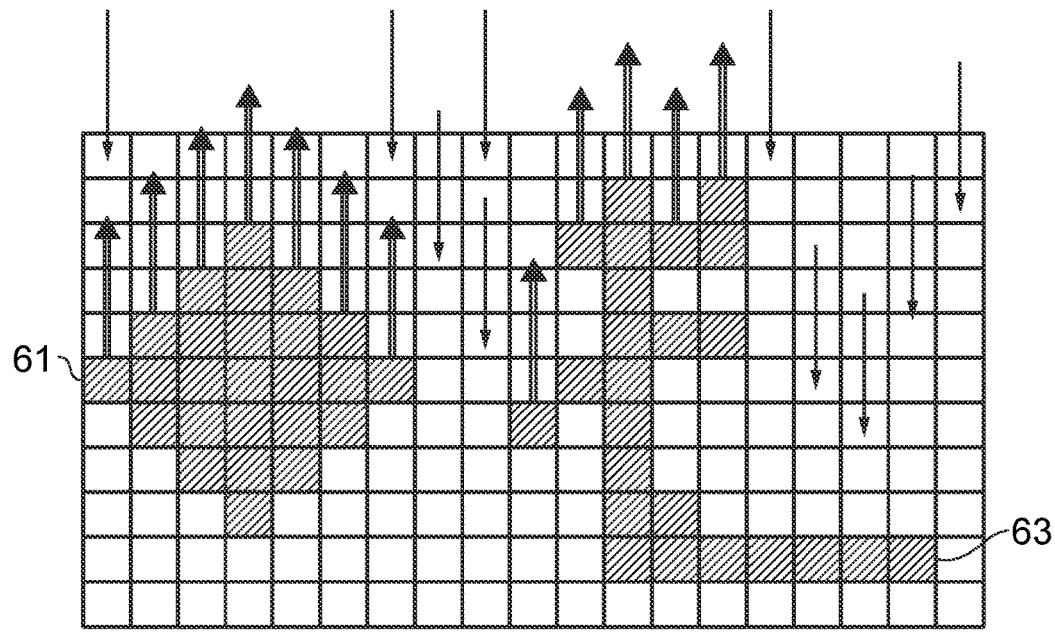
Figure 7:
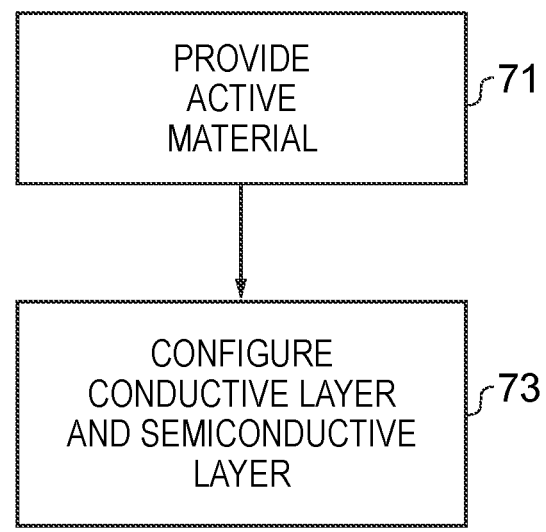

For a better understanding of various examples that are useful for understanding the detailed description, reference will now be made by way of example only to the accompanying drawings in which:

FIG. 1 illustrates an example apparatus;
FIG. 2 illustrates an example apparatus;
FIG. 3 illustrates example apparatus;
FIG. 4 illustrates an example device comprising a plurality of apparatus;
FIGS. 5A and 5B illustrate example arrays;
FIGS. 6A and 6B; illustrate example arrays; and
FIG. 7 illustrates a method.

DETAILED DESCRIPTION

The Figures illustrate an apparatus 1 comprising: an active material 5 positioned between a semiconductive layer 3 and a conductive layer 7; wherein the semiconductive layer 3 and the conductive layer 7 are configured such that in a first mode of operation the active material 5 acts as a photon emitter and in a second mode of operation the active material 5 acts as a photon detector.

The apparatus 1 may provide an integrated photon emitter and photon detector. The apparatus 1 may be arranged in an array 43 comprising a plurality of other apparatus. The array 43 may have a high resolution which may enable improved imaging. The array 43 may have a configurable pattern of photon emitters and photon detectors which may also enable improved imaging. In some examples the apparatus 1 may be used to enable biometric parameters to be monitored.

FIG. 1 schematically illustrates an example apparatus 1. The apparatus 1 comprises a semiconductive layer 3, an active material 5 and a conductive layer 7.

The active material 5 is positioned between the semiconductive layer 3 and the conductive layer 7. The active material 5 may comprise any material which may be configured for both photon emission and photon detection. The apparatus 1 may be arranged so that the active material 5 is arranged for photon emission at a first time and photon detection at a second, different time. Whether the active material 5 is configured for photon emission or photon detection may be determined by how the semiconductive layer 3 and the conductive layer 7 are activated.

In some examples the active material 5 may comprise quantum dots. The quantum dots may act as a source of photons in a first mode of operation and as photon detectors in a second mode of operation.

Other materials may be used as the active material 5 in other examples of the disclosure. For instance in other examples the active material 5 could comprise a light emitting polymer, a J-aggregate dye or any other suitable material.

The active material 5 may be provided overlaying the semiconductive layer 3. The semiconductive layer 3 may comprise any conductive material. In some examples the semiconductive layer 3 may comprise a carbon based material such as graphene, graphene oxide, carbon nanotubes, or any other suitable material.

The semiconductive layer 3 may be configured to enable charge transfer between the semiconductive layer 3 and the active material 5. The semiconductive layer 3 may be configured such that charges produced by incident photons within the active material 5 are transferred to the semiconductive layer 3. These charges may change the conductivity of the semiconductive layer 3.

In some examples the active material 5 may be provided directly overlaying the semiconductive layer 3 so that there is no intervening material between the semiconductive layer 3 and the active material 5. In other examples one or more layers may be provided between the semiconductive layer 3 and the active material 5. For example, in some apparatus 1, a hole injection layer may be provided between the semiconductive layer 3 and the active material 5. The hole injection layer may enable positive charge to be transferred between the semiconductive layer 3 and the active material 5.

The conductive layer 7 is provided overlaying the active material 5. The conductive layer 7 may comprise a transparent conductive material such as indium tin oxide (ITO), fluorine doped tin oxide (FTO), aluminium doped zinc oxide (AlZnO). In other examples the transparent conductive material may comprise poly(2,3-dihydrothieno-1,4-dioxin)-poly(styrenesulfonate)(PEDOT:PSS), polypyrrole (Ppy), silver nanowires, carbon nanotubes, graphene-based materials including composites thereof, graphene or any other suitable material. The conductive layer 7 may be transparent to enable photons to be detected and emitted by the active material 5.

The conductive layer 7 may be configured to enable an electric field to be provided between the semiconductive layer 3 and the conductive layer 7. The active material 5 may be positioned within the electric field.

In some examples one or more layers may be provided between the active material 5 and the conductive layer 7. For example, in some apparatus 1, a dielectric material may be provided overlaying the active material 5 to passivate the active material 5. In some apparatus 1 an electron transport layer may be provided to enable negative charge to be transferred between the active material 5 and the conductive layer 7.

FIG. 2 illustrates an example apparatus 1 in more detail. The example apparatus 1 comprises a substrate 21, a field effect transistor 23 and an overlaying electrode 25. The substrate 21 may provide means for supporting the components of the apparatus 1. The components of the apparatus 1 may be printed on the substrate 21. In some examples the substrate 21 may comprise a flexible material.

The substrate 21 may be made of any suitable material. In some examples the substrate 21 may comprise an insulating material. For instance the substrate 21 could comprise glass, silicon, quartz, polyethylene 2, 6-naphthalate (PEN). polyethylene terephthalate (PET), polyimide (PI), polycarbonate (PC), polyethylene (PE), polyurethane (PU), polymethylmethacrylate (PMMA), polystyrene (PS), natural rubbers such as; polyisoprenes, polybutadienes, polychloraprenes, polyisobutylenes, nitrile butadienes and styrene butadienes, saturated elastomeric materials such as; polydimethylsiloxane (PDMS), silicone rubbers, fluorosilicone rubbers, fluoroelastomers, perfluoroelastomers, ethylene vinyl acetate (EVA) thermoplastic elastomers such as styrene block copolymers, thermoplastic polyolefins, thermoplastic vulcanisates, thermoplastic polyurethane (TPU) thermoplastic copolyesters, melt processable rubbers or any other suitable material.

In other examples the substrate 21 could comprise a conductive material such as a metal foil. The metal foil may comprise a planarised metal foil. The field effect transistor 23 may be created on the metal foil.

Only one apparatus 1 is shown in the example of FIG. 2 it is to be appreciated that in other examples a plurality of apparatus 1 may be provided on the same substrate 21.

The example apparatus 1 of FIG. 2 also comprises a field effect transistor 23. The field effect transistor 23 may be configured to enable the apparatus 1 to detect photons. The field effect transistor may be provided on the substrate 21. The field effect transistor 23 may be a thin film transistor, graphene field effect transistor or any other suitable type of transistor.

The field effect transistor 23 comprises a source electrode 11, a gate electrode 13 and a drain electrode 15. In the example of FIG. 2 the electrodes 11, 13, 15 are provided within a planarization layer 27. The planarization layer 27 may be made of any suitable insulating material. The electrodes 11, 13, 15 may be made of any suitable conductive material.

A semiconductive layer 3 connects the source electrode 11 and the drain electrode 15 to provide a channel with the field effect transistor 23. The semiconductive layer 3 is coupled to the active material 5 so that when the apparatus 1 is in a detecting mode of operation the resistivity of the semiconductive layer 3 is dependent upon the photons detected by the active material 5. The semiconductive layer 3 may comprise a layer of carbon based materials such as graphene, graphene oxide or carbon nanotubes. Other materials may be used in other examples of the disclosure.

In the example of FIG. 2 a dielectric layer 19 is provided between the planarization layer 27 and the semiconductive layer 3. The dielectric layer 19 may be provided between the gate electrode 13 and the semiconductive layer 3. The dielectric layer 19 may comprise an insulating oxide material such as $SiO_2$, LiF, $Si_3N_4$, alumina, titania, hafnium oxide or any other suitable material.

A layer of active material 5 is provided overlaying the semiconductive layer 3. The active material 5 may be tuned to detect and emit photons within a range of wavelengths. For instance where the apparatus 1 is being used to monitor biometric parameters the apparatus 1 may be tuned to detect and emit photons in the infra red frequency range.

In some examples the layer of active material 5 may comprise a layer of quantum dots. The quantum dots may be deposited on the semiconductive layer 3.

The quantum dots may comprise nanocrystals which may be configured to produce electric charge in response to incident photons. The quantum dots may also be configured to emit photons in response to charge transferred to the quantum dots or an electric field applied to the quantum dots.

The quantum dots may be provided in a very thin layer. In some examples the quantum dot layer may be a monolayer and so may be effectively two dimensional. In some examples the thickness of the quantum dot layer may be of the order of 200 mm. Having a thin layer may allow for optimal charge transfer between the quantum dots and the semiconductive layer 3.

The quantum dots may be configured to be sensitive to a particular frequency of electromagnetic radiation. In some examples the quantum dots may be configured to be sensitive to infra red radiation. In such examples the materials used for the quantum dots may comprise: CdSe, CdS, PbSe, PbS, ZnO, ZnS, CZTS, $Cu_2S$, $Bi_2S_3$, $Ag_2S$, HgTe, CdTe, CdHgTe, HgZnTe, CdZnTe, InAs, InSb, Ge, CIS, CIGS or any other suitable material.

The size of the quantum dots which are used may be dependent upon the material which is used and the wavelength of light which is to be detected.

In some examples a ligand may be provided to connect the quantum dots to each other. The ligand may also be configured to connect the quantum dots to the semiconductive layer 3. The ligand may be configured to cross link the quantum dots so that they form a conductive solid. The ligand may comprise any suitable material or combinations of material such as ethanedithiol, ethylene diamine, ethanethiol, propanethiol, benzenedithiol, thioglycerol, dithioglycerol, hydrazine, formic acid, oxalic acid, acetic acid, or inorganic moieties such as $SnS_4$, $PbBr_2$, $PbI_2$, $PbCl_2$ or any other suitable material.

The coupling of the quantum dots to the semiconductive layer 3 enables excitons generated in the quantum dots to be separated into electron-hole pairs and either the holes or electrons are transferred to the semiconductive layer 3.

In some examples the quantum dot active material 5 may comprise an additional photosensitive semiconductor material. The additional photosensitive semiconductor material may increase the photosensitivity of the quantum dot active material 5. The additional photosensitive semiconductor material may comprise a conjugated polymer or dye or any other suitable material.

The quantum dot active material 5 may have very high levels of quantum efficiency. The quantum efficiency quantum dot active material 5, particularly at infra red wavelengths may enable measurements to be made over large areas with low power input.

A further dielectric layer 17 is provided overlaying the active material 5. The further dielectric layer 17 may be configured to provide a passivation layer for the active material 5. The further dielectric layer 17 may comprise any suitable material such as insulating oxide material such as $SiO_2$, $Si_3N_4$, LiF, alumina, titania, hafnium oxide or any other suitable material.

The conductive layer 7 is provided overlaying the further dielectric layer 17. The conductive layer 7 may provide an overlaying electrode 25. The overlaying electrode 25 may comprise a transparent conductive material. In some examples the transparent conductive material may comprise a conducting metal oxide such as Indium Tin Oxide (ITO), Fluorine doped tin oxide (PTO), Aluminium doped zinc oxide (AlZnO). In other examples the transparent conductive material may comprise poly(2,3-dihydrothieno-1,4-dioxin)-poly(styrenesulfonate)(PEDOT:PSS), polypyrrole (Ppy), silver nanowires, carbon nanotubes, graphene based materials including composites thereof, graphene or any other suitable material.

The conductive layer 7 is connected to a power source 29 to enable an electric field to be applied between the semiconductive layer 3 and the conductive layer 7. This enables an electric field to be applied to the active material 5.

The apparatus 1 can be operated in a first mode of operation or in a second mode of operation. The apparatus 1 may be controlled so that it can operate in either the first mode of operation or the second mode of operation. The apparatus 1 may be controlled to switch between different modes of operation so that the apparatus 1 can operate in the first mode of operation at a first time and in a second mode of operation at a second different time.

In the first mode of operation an electric field is applied between the semiconductive layer 3 and the conductive layer 7. The applied electric field may be an alternating electric field. The source electrode 11 and the drain electrode 15 may be shorted. In some examples the applied electric field may enable current to be driven between the semiconductive layer 3 and the conductive layer 7 through the active material 5. The applied electric field may enable photons to be emitted by the active material 5.

In the second mode of operation the semiconductive layer 3 is connected to the source electrode 11 and the drain electrode 15 such that the semiconductive layer 3 provides a channel within the field effect transistor 23. When photons are incident on the active material 5 the active material 5 absorbs the photons and causes charge to be transferred to the semiconductive layer 3. This provides a channel with a resistance dependent on the detected photons.

In the second mode of operation the conductive layer 7 may be disconnected from the power source 29 so that no electric field is provided by the conductive layer 7.

Therefore the apparatus 1 may be used as either a photon detector or a photon emitter depending on the configuration of the semiconductive layers 3 and the conductive layer 7 within the apparatus 1.

It is to be appreciated that modifications and variations could be made to the example apparatus of FIG. 2. For instance in some example apparatus 1 the dielectric layers 17, 19 could be replaced with hole injection layers and electron transport layers. In some examples a hole injection layer may be provided between the active material 5 and the semiconductive layer 3 and an electron transport layer may be provided between the active material 5 and the conductive layer 7. The materials which are used as hole injection layers and electron transport layers may depend on the work function of the quantum dots and the semiconductive layer 3. In some examples the hole injection layers and electron transport layers could comprise materials such as PEDOT/PSS (poly(3,4-ethylenedioxythiophene) polystyrene sulfonate), PVK (poly N-vinyl carbazole), ZnO nanoparticles or any other suitable material. In such examples the hole injection layers and electron transport layers may enable current to be driven through the device when the apparatus 1 is in the first mode of operation and an electric field is applied between the semiconductive layer 3 and the conductive layer 7.

In some examples a hole injection layer and/or an electron transport layer may be provided within the apparatus 1 to create a bias within the apparatus 1. For example, in some apparatus 1 the active material 5 may transfer holes to the semiconductive layer 3 in response to detected photons. Such apparatus 1 may comprise an active material 5 comprising PbS quantum dots and a semiconductive layer 3 comprising graphene. In such apparatus 1 an electron transport layer may be provided as passivation layer overlaying the active material 5. The electron transport layer may assist in removing negative charge from the active material 5 when the apparatus 1 is detecting photons.

In the above described example apparatus 1 the active material comprises quantum dots. It is to be appreciated that in other examples other materials could be used. For instance, in some examples the active material 5 could comprise materials such as polyfluorenes, polyphenylene vinylenes, organic transition metal complexes or any other suitable materials.

In some examples the active material 5 may comprise an organic photovoltaic layer. The organic photovoltaic layer may comprise n-type materials, or p-type materials, or a mixture of both n-type and p-type materials. Examples of p-type materials which may be used comprise polythiophene, polypyrrole, polyaniline, polyfluorene, polyphenylene vinylene, polyphenylene. Examples of n-type materials which could be used comprise fullerenes, dithieno [3, 2-b:2', 3'-d]pyrrole (DTP), poly('substituted dithieno[3, 2-b: 2', 3'-d]pyrrole)s (PDTPs).

In some examples a microlens 9 could be provided overlaying the apparatus 1, as shown in FIG. 1. The microlens may be configured to direct light substantially perpendicular to surface of the apparatus 1 when the apparatus 1 is in an emitting mode of operation. The microlens may also be configured to direct light towards the centre of the apparatus 1 when the apparatus is in a detecting mode of operation.

In examples where a plurality of apparatus 1 are provided a fiber optic faceplate (also referenced as 9 in FIG. 1) may be provided overlaying the plurality of apparatus 1. The fiber optic faceplate would direct light in the same or similar manner to a microlens. The fiber optic faceplate may also prevent a lateral spread of light to adjacent pixels and so may reduce cross talk between adjacent emitting and detecting pixels.

The apparatus 1 may be small. In some examples the apparatus 1 may have a lateral dimensions of the order of 10-100 μm. A plurality of such apparatus 1 may be coupled together to form an array 43 as described below. The array 43 may be arranged to provide very high spatial resolution.

FIG. 3 illustrates two example apparatus 1 positioned adjacent to each other. The example apparatus 1 each comprise a semiconductive layer 3 an active material 5 and a conductive layer 7 which may be as described above. The apparatus 1 are mounted on the substrate 21. The apparatus 1 may form part of an array 43 comprising a plurality of identical and/or similar apparatus 1.

In the example of FIG. 3 a barrier 31 is provided between the adjacent apparatus 1. In the example of FIG. 3 the barrier 31 extends above the height of the conductive layer 7. The barrier 31 may be arranged to prevent light emitted from a first apparatus 1 from causing interference at a second apparatus 1.

In the example of FIG. 3 the barriers 31 may be formed from the source electrode 11 and the drain electrode 15. In such examples each apparatus 1 may comprise a barrier 31 at either side of the apparatus 1. This may provide two barriers 31 between each adjacent pair of apparatus 1. In some examples one electrode 11, 15 could be shared between adjacent apparatus 1.

In the example apparatus of FIG. 3 the electrodes 11, 15 may be used to enable the photons to be detected and also to prevent interference between apparatus 1. Using the same components to perform a plurality of functions may enable the size of the apparatus 1 to be reduced. This may also enable the spacing between adjacent apparatus 1 to be reduced. This may enable an array 43 of apparatus 1 to be configured to provide with high spatial resolution imaging. This may also enable reduced cross talk between adjacent apparatus 1 within the array 43.

FIG. 4 illustrates an example device 41 comprising a plurality of apparatus 1. The example device 41 comprises an array 43 comprising a plurality of apparatus 1 and control circuitry 45.

The array 43 comprises a plurality of apparatus 1. The plurality of apparatus 1 within the array 43 may be as described above. The modes of operation of the apparatus 1 within the array 43 may be controlled by the control circuitry 45.

The plurality of apparatus 1 may be arranged in to different subsets. A first subset of the plurality of apparatus 1 may be configured in the first mode of operation so that the first subset are configured to act as photon emitters. This may enable a first portion of the array 43 to act an emitter. A second subset of the plurality of apparatus 1 may be configured in the second mode of operation so that the second subset of apparatus 1 are configured to act as photon detectors. This may enable a second portion of the array 43 to act as a detector.

The control circuitry 45 may control the array 43 so that an apparatus 1 may be arranged in different subsets at different times. At a first time an apparatus 1 may act as a photon emitter and at a second time an apparatus 1 may act as a photon detector. This may enable different portions of the array 43 to act as detectors and emitters at different time.

FIGS. 5A to 6B illustrate example arrays 43 and different configurations for these arrays.

In the example device 41 of FIG. 4 the control circuitry 45 may be configured to address any of the apparatus 1 within the array 43 and control which apparatus 1 are configured in a first mode of operation and which apparatus 1 are configured in a second mode of operation.

The control circuitry 45 may comprise processing circuitry 47 and memory circuitry 49. The processing circuitry 47 may be configured to read from and write to memory circuitry 49. The processing circuitry 47 may comprise one or more processors. The processing circuitry 47 may also comprise an output interface via which data and/or commands are output by the processing circuitry 47 and an input interface via which data and/or commands are input to the processing circuitry 47.

The memory circuitry 49 may be configured to store a computer program 51 comprising computer program instructions (computer program code 53) that controls the operation of the apparatus 1 within the array 43 when loaded into processing circuitry 47. The processing circuitry 47 by reading the memory circuitry 49 is able to load and execute the computer program 51.

The computer program 51 may arrive at the device 41 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 51. The apparatus may propagate or transmit the computer program 51 as a computer data signal. In some examples the computer program code 53 may be transmitted to the device 61 using a wireless protocol such as Bluetooth, Bluetooth Low Energy, Bluetooth Smart, 6LoWPan (IP$_v$6 over low power personal area networks) ZigBee, ANT+, near field communication (NFC), Radio frequency identification, wireless local area network (wireless LAN) or any other suitable protocol.

Although the memory circuitry 49 is illustrated as a single component in the figures it is to be appreciated that it may be implemented as one or more separate components some or all of which may be integrated/removable and/or may provide permanent/semi-permanent/dynamic/cached storage.

Although the processing circuitry 47 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

It is to be appreciated that the example device 41 may comprise other feature which are not illustrated in FIG. 4 for instance, in some examples the device 41 may be a wearable device 41 which may be configured to be worn by a user. In such examples the device 41 may be configured to monitor biometric parameters of a user. In such examples the device 41 may also comprise attachment means which may enable the device 41 to be secured to the user's body. In such examples the device 41 may be configured so that when the device 41 is attached to the body of a user the array 43 is adjacent to the skin of the user. This may enable the apparatus 1 within the array to be used to illuminate a portion of the user's body and measure the light absorbed by that portion.

FIGS. 5A and 5B illustrate example arrays 43 which may be used in some example devices 41. In the example of FIGS. 5A and 5B apparatus 1 which are configured in an emitting mode of operation have darker shading and apparatus 1 which are configured in a detecting mode have lighter shading.

The example array 43 of FIGS. 5A and 5B comprises a plurality of apparatus 1 arranged in rectangular array 43. The array 43 comprises a plurality of rows and a plurality of columns orthogonal to the rows.

FIGS. 5A and 5B illustrate the same example array 43 at two different points in time. In the example of FIG. 5A all of the apparatus 1 are configured as detectors. The control circuitry 5 may provide a control signal to configure all of the apparatus in the detecting mode of operation.

At a different point in time all of the apparatus 1 are configured as emitters, as illustrated in FIG. 5B. The control circuitry 5 may provide a control signal to configure all of the apparatus in the emitting mode of operation.

The example arrangement of FIGS. 5A and 5B may provide an array 43 with very high resolution. As all of the apparatus 1 can be configured as detectors. There is no need to provide emitting apparatus 1 between the detecting apparatus 1. This can provide a reduced separation between the detecting apparatus 1 and improve the resolution of the array 43. Also, as all of the apparatus 1 may be used as emitters this may provide an increased amount of light. This may improve the efficiency and accuracy of the array 43.

FIGS. 6A and 6B illustrate a similar array 43 in different configurations. In the examples of FIGS. 6A and 6B the array 43 is configured to provide both photon emitters and photon detectors simultaneously. The control circuitry 45 is configured to provide a control signal to the array 43 to control which apparatus 1 are configured in an emitting mode and which apparatus 1 are configured in a detecting mode.

In the example of FIG. 6A the array 43 is configured so that a first row comprises only detecting apparatus 1. A second row, which is adjacent to the first row, comprises alternating emitting and detecting apparatus 1. This pattern is repeated across the array 43. This provides a regular pattern of emitters and detectors across the array 43. This may provide an even illumination and detection across the array 43.

FIG. 6B shows an array 43 in a different configuration. The array 43 could be the same array of FIG. 6A at a different point in time. In the example of FIG. 6B the apparatus 1 are arranged to focus the emission of photons on particular locations.

In FIG. 6B the array 43 comprises a first emitting portion 61. The first emitting portion 61 comprises a cluster of apparatus and may enable a designated area to be illuminated. The array 43 also comprises a second emitting portion 63. The second emitting portion 63 may be shaped to correspond to a feature which is to be illuminated. The feature could comprise a biometric feature of a user such as a vein or artery.

The shapes and arrangements of the emitting portions 61, 63 may change at different times so that the same array 43 may be used to monitor or illuminate different features.

In the examples of FIGS. 5A to 6B the arrays 43 are linear. It is to be appreciated that in other examples non-linear arrays 43 may be used. In such examples the apparatus 1 may be arranged in a non-linear arrangement such as spirals, concentric circles, curvilinear arrangements or any other suitable arrangement. In some examples the shapes of the apparatus 1 may be arranged to maximise the area covered. For instances in the linear arrays of FIGS. 5A to 6B apparatus 1 are rectangular. In non-linear arrangements the apparatus 1 may be circular, triangular, hexagonal, rhombic, rectangular or any other shape.

In some examples all of the apparatus 1 within an array 43 may be configured to emit and/or detect photons at the same wavelength. In other examples the different apparatus 1 may be configured to emit and/or detect photons at different wavelengths.

FIG. 7 illustrates a method. The method may be implemented using apparatus 1 and devices 41 as described above. The method comprises, at block 71, providing an active material 5 between a semiconductive layer 3 and a conductive layer 7. The method also comprises, at block 73, configuring the semiconductive layer 3 and the conductive layer 7 such that in a first mode of operation the active material acts 5 as a photon emitter and in a second mode of operation the active material 5 acts as a photon detector.

Examples of the disclosure provide for an apparatus 1 that can be configured as both a photon emitter and a photon detector. The apparatus 1 may be configured to operate as a detector or an emitter at different times. This may enable the apparatus 1 to be switched between different modes of operation as needed. This may provide for an array of apparatus 1 which can be configured into any suitable arrangement of emitters and detectors.

In some examples the array 43 may be configured to enable biometric features of the user to be monitored and/or identified. For instance the array 43 could be used to measure heart rate, heart rate variability, blood oxygenation level, blood pressure or other diffuse optical property of human tissue. As the apparatus 1 within the array 43 can be easily reconfigured as either emitters or photon detectors this may enable the array to be configured to correlate to the biometric features of the user. In some examples the biometric features may enable biometric parameters of the user to be monitored. In some examples the biometric features may comprise blood vessels, veins, arteries or capillaries, or specific regions of healthy tissue or damaged tissue such as melanoma, or wounds.

In some examples the devices 41 may be configured to provide a series of first illumination points with a first spacing followed by a series of second illumination points at a second spacing. Such an arrangement could be used to measure a time delay in a user's pulse. Such measurements could be used to calculate a user's blood pressure.

In some examples the device 41 could be configured to provide phototherapy or other treatment to a user. As the array 43 is configurable and also may have a high resolution this may enable the photo therapy be targeted towards the area of the user which requires treatment, for instance a wound or lesion.

It is to be appreciated that example apparatus 1 and devices 41 could be used in applications other than those described above. In particular the apparatus 1 could be used in applications other than the measurement or monitoring of biometric parameters.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this detailed description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
a material positioned between a semiconductive layer and a conductive layer;
wherein the semiconductive layer comprises graphene and the graphene forms a graphene field effect transistor; and
wherein the semiconductive layer and the conductive layer are configured such that in a first mode of operation the material acts as a photon emitter and in a second mode of operation the material acts as a photon detector.

2. An apparatus as claimed in claim 1 wherein in the first mode of operation an electric field is applied between the semiconductive layer and the conductive layer.

3. An apparatus as claimed in claim 1 wherein the semiconductive layer is connected to a source electrode and a drain electrode such that in the second mode of operation the semiconductive layer provides a channel within a field effect transistor.

4. An apparatus as claimed in claim 1 wherein the semiconductive layer and the conductive layer are arranged such that the apparatus can be configured in the first mode of operation at a first time and in the second mode of operation at a second, different time.

5. An apparatus as claimed in claim 1 wherein the material comprises quantum dots.

6. An apparatus as claimed in claim 1 wherein a dielectric layer is provided between the material and the conductive layer.

7. An apparatus as claimed in claim 1 wherein a hole transport layer is provided between the material and the semiconductive layer.

8. An apparatus as claimed in claim 1 wherein an electron transport layer is provided between the material and the conductive layer.

9. An apparatus as claimed in claim 1 comprising at least one of a barrier, a microlens array or fiber optic faceplate configured to prevent illumination from an adjacent apparatus.

10. An apparatus as claimed in claim 1 comprising control circuitry configured to control the mode of operation of the apparatus.

11. An array comprising a plurality of apparatus, at least one of the plurality of apparatus respectively comprising:
a material positioned between a semiconductive layer and a conductive layer;
wherein the semiconductive layer comprises graphene and the graphene forms a graphene field effect transistor; and
wherein the semiconductive layer and the conductive layer are configured such that in a first mode of operation the material acts as a photon emitter and in a second mode of operation the material acts as a photon detector.

12. An array as claimed in claim 11 wherein a first subset of one or more of the plurality of apparatus are configured in the first mode of operation and a second subset of one or more of the plurality of apparatus are configured in the second mode of operation.

13. An array as claimed in claim 12 wherein at least one apparatus can be arranged within different subsets at different times.

14. A method comprising:
providing a material between a semiconductive layer and a conductive layer;
wherein the semiconductive layer comprises graphene and the graphene forms a graphene field effect transistor; and
configuring the semiconductive layer and the conductive layer such that in a first mode of operation the material acts as a photon emitter and in a second mode of operation the material acts as a photon detector.

15. A method as claimed in claim 14, wherein in the first mode of operation an electric field is applied between the semiconductive layer and the conductive layer.

16. A method as claimed in claim 14, wherein the semiconductive layer is connected to a source electrode and a drain electrode such that in the second mode of operation the semiconductive layer provides a channel within a field effect transistor.

17. A method as claimed in claim 14, further comprising configuring the material in the first mode of operation at a first time and in the second mode of operation at a second, different time.

18. A method as claimed in claim 14, wherein the material comprises quantum dots.

19. A method as claimed in claim 14, further comprising providing a dielectric layer between the material and the conductive layer.

20. A method as claimed in claim 14, further comprising providing a hole transport layer between the material and the semiconductive layer.

* * * * *